United States Patent [19]
Abatjoglou et al.

[11] 4,429,161
[45] Jan. 31, 1984

[54] PROCESS FOR PREPARING ORGANIC TERTIARY POLYPHOSPHINE MONOOXIDES

[75] Inventors: Anthony G. Abatjoglou, Charleston; Louis A. Kapicak, Cross Lanes, both of W. Va.

[73] Assignee: Union Carbide Corporation, Danbury, Conn.

[21] Appl. No.: 293,145

[22] Filed: Aug. 17, 1981

[51] Int. Cl.$^3$ .............................................. C07F 9/53
[52] U.S. Cl. ......................................... 568/14; 568/9; 568/10; 568/11; 568/15; 556/404; 564/15; 548/413
[58] Field of Search ................... 568/14, 15, 9, 10, 11; 556/404; 564/15; 260/326.2, 326.8

[56] References Cited

U.S. PATENT DOCUMENTS

| | | | |
|---|---|---|---|
| 3,325,546 | 6/1967 | Hays | 568/14 |
| 3,426,021 | 2/1969 | Seyferth | 260/246 |
| 3,742,064 | 6/1973 | Diamond et al. | 568/15 |
| 3,975,447 | 8/1976 | Knoth, Jr. et al. | 568/14 |
| 4,289,809 | 8/1981 | Traynor et al. | 568/10 X |
| 4,298,541 | 11/1981 | Oswald et al. | 260/429 R |
| 4,302,401 | 11/1981 | Oswald | 260/448 |

FOREIGN PATENT DOCUMENTS

| | | | |
|---|---|---|---|
| WO80/01690 | 8/1980 | PCT Int'l Appl. | 260/429 R |
| 154860 | 7/1962 | U.S.S.R. | 568/14 |
| 258309 | 4/1970 | U.S.S.R. | 568/14 |

OTHER PUBLICATIONS

"J. Amer. Chem. Soc." vol. 87, pp. 671-673 (1965), by A. M. Aguiar et al.
"Inorganic Chemistry" vol. 14, pp. 650-660 (1975), by S. O. Grim et al.
J. Amer. Chem. Soc., vol. 81, pp. 3806-3807 (1959) by M. Zanger et al.

Primary Examiner—Helen M. S. Sneed
Attorney, Agent, or Firm—Reynold J. Finnegan

[57] ABSTRACT

Process for producing organic tertiary polyphosphine monooxides which comprises reacting an organic tertiary polyphosphine with an organic monofunctional alkylating agent to form an intermediate monophosphonium salt of the polyphosphine starting material and then hydrolyzing the salt so produced to the desired polyphosphine monooxide product.

11 Claims, No Drawings

PROCESS FOR PREPARING ORGANIC TERTIARY POLYPHOSPHINE MONOOXIDES

BACKGROUND OF THE INVENTION

This invention relates to a process for preparing monooxides of organic tertiary polyphosphines. More particularly this invention relates to a process for preparing highly selective yields of organic tertiary polyphosphine monooxides.

Heretofore prior art methods of converting tertiary polyphosphines to phosphine oxides using oxidizing agents such as hydrogen peroxide, organic hydroperoxides, oxygen and the like have lead to non-selective oxidations and the formation of statistically expected mixtures of unoxidized, monooxidized, dioxidized, etc., tertiary polyphosphines.

SUMMARY OF THE INVENTION

It has now been discovered that tertiary polyphosphines can be highly selectively converted to tertiary polyphosphine monooxides. Thus it is an object of this invention to provide a process for preparing organic tertiary polyphosphine monooxides. It is another object of this invention to provide a process for preparing highly selective yields of bisphosphine monooxides from organic tertiary bisphosphines. Other objects and advantages of this invention will become readily apparent from the following written description and appended claims.

Accordingly the generic aspect of this invention can be described as a process for producing an organic tertiary polyphosphine monooxide which comprises reacting a tertiary polyphosphine compound having the general formula

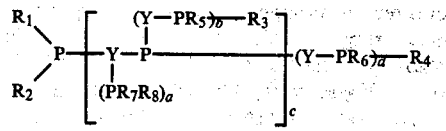

wherein each $R_1$, $R_2$, $R_3$, $R_4$, $R_5$, $R_6$, $R_7$ and $R_8$ represent an identical or different substituted or unsubstituted monovalent hydrocarbon radical, wherein each Y represents an identical or different organic bridging group, wherein a, b and d each represent a value of zero or 1, and wherein c represents an integer of from 1 to 3; with an organic monofunctional alkylating agent to form a monophosphonium salt of said organic tertiary polyphosphine compound; hydrolyzing said salt compound with an aqueous alkaline solution to form an organic tertiary polyphosphine monooxide product wherein the oxygenated phosphorous atom of said monooxide product corresponds to the alkylated phosphorus atom of said monophosphonium salt, and recovering the monooxide product so produced.

More preferably this invention can be described as a process for preparing an organic tertiary bisphosphine monooxide compound having the general formula

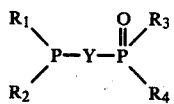

wherein each $R_1$, $R_2$, $R_3$, $R_4$ and Y are as defined above, said process comprising reacting a tertiary bisphosphine compound having the general formula

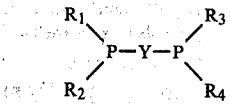

wherein $R_1$, $R_2$, $R_3$, $R_4$ and Y are as defined above, with an organic monofunctional alkylating agent to form a monophosphonium salt of said organic tertiary bisphosphine compound; hydrolyzing said salt compound with an aqueous alkaline solution to form said organic tertiary bisphosphine monooxide, and recovering the monooxide product so produced.

DESCRIPTION OF THE PREFERRED EMBODIMENTS

As seen above, the process of this invention relates to a two-step process involving the conversion of a tertiary polyphosphine to a monophosphonium salt of said polyphosphine followed by the hydrolysis of said salt to a tertiary polyphosphine monooxide product.

The subject process is indeed unique in that step one of the process of this invention which is carried out in the presence of a solvent produces an insoluble monophosphonium salt precipitate thus virtually avoiding dialkylation of the polyphosphine starting material by the organic monofunctional alkylating agent and insuring the formation of a highly selective yield of desired polyphosphine monooxide product upon hydrolysis of the intermediate monophosphonium salt. Thus the starting organic tertiary polyphosphine is nearly quantitatively converted to an intermediate monophosphonium salt which can be easily isolated and recovered from the solvent by any suitable conventional method, such as by filtration, and the like. If desired the monophosphonium salt can be washed with clean solvent and even recrystallized for further purification. In addition any unreacted organic tertiary polyphosphine starting material remains in the solvent and can be recovered and recycled, if desired.

The reaction conditions of step one of the process of this invention are not narrowly critical and can be varied widely with regard to reaction temperature, reaction solvent, concentrations and types of reactants employed.

The reaction solvent can be any suitable organic solvent in which the solid organic tertiary polyphosphine starting material is soluble and liquid organic monofunctional alkylating agent is miscible and in which their reaction product (i.e. monophosphonium salt) is insoluble. Illustrative solvents include e.g. hydrocarbons, such as toluene, benzene, hexane, and the like; halohydrocarbons such as chloroform, methylene chloride, chlorobenzene, and the like; ethers such as dibutylether, bis-(2-ethoxyethyl) ether, and the like; ketones, such as acetone, methylethylketone and the like. However dipolar aprotic solvents such as dimethyl formamide, dimethyl sulfoxide, acrylonitrile, etc. as well as hydroxylic solvents such as alcohols and organic acids should preferably be avoided since significant solubility of the intermediate monophosphonium salt can lead to its further reaction to form diphosphonium salts and thus decrease the efficiency of the process of this invention. Likewise hydroxylic solvents can preferentially react with some organic monofunctional alkylating agents e.g. organic halides. Accordingly the preferred organic solvent is an inert solvent, especially a hydrocarbon solvent. The amount of solvent employed is not narrowly critical and need only be that amount which is at least sufficient to solubilize that amount of solid tertiary polyphosphine starting material employed. In general amounts of solvent ranging from about 5 to about 1000 liters and preferably from about 10 to about 100 liters per mole of organic tertiary polyphosphine starting material should be sufficient for most purposes.

The reaction of step one of the process of this invention can be carried out at any suitable temperature which is normally dictated by the reactivity of the organic monofunctional alkylating agent and organic tertiary polyphosphine starting material. Moreover the reaction can be carried out at sub, atmospheric or elevated pressures, as desired and in any suitable reaction vessel desired. In general the reaction temperature may vary from about ambient temperature to the boiling point of the particular solvent employed. Temperatures of from about 20° C. to about 200° C. should be suitable in most instances, the present preferred temperature being from about 60° C. to about 120° C. Moreover, while the reaction may be carried out in air, it is preferably carried out in an inert gas atmosphere such as nitrogen, since in solution phosphine compounds can be slowly air oxidized to phosphine oxides. It is further preferred to thoroughly mix the reactants involved and such can be done by any conventional means such as by stirring, and the like. The general reaction is fairly rapid and its progress and completion followed in any suitable manner such as by thin layer chromatographic monitoring of the consumption of the polyphosphine starting material and by the visual formation of the monophosphonium salt precipitate that is insoluble in the solvent employed, which precipitated salt can be easily recovered as described above.

The organic tertiary polyphosphine starting materials of the process of this invention are those having the general formula

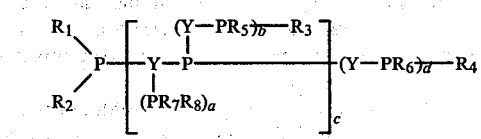

wherein $R_1$ to $R_8$, Y and a, b, c and d are as defined herein. Such types of polyphosphine starting materials and/or methods for their preparation are well known in the art. Among the more preferred illustrative types of polyphosphine starting materials are those having the following formulas:

$R_1R_2PYPR_3R_4$

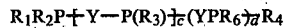

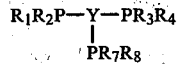

and the like. The most preferred polyphosphine starting materials are bisphosphines of the formula $R_1R_2PYPR_3R_4$.

Monovalent hydrocarbon radicals represented by $R_1$, $R_2$, $R_3$, $R_4$, $R_5$, $R_6$, $R_7$ and $R_8$ in the above formulas include those containing from 1 to 30 carbon atoms such as substituted or unsubstituted alkyl, aryl, alkaryl, aralkyl and alicyclic radicals. Among the more specific unsubstituted monovalent hydrocarbon radicals that may be mentioned are alkyl radicals including primary, secondary and tertiary alkyl radicals such as methyl, ethyl, n-propyl, isopropyl, butyl, sec-butyl, t-butyl, t-butylethyl, t-butylpropyl, n-hexyl, amyl, sec-amyl, t-amyl, iso-octyl, decyl, dodecyl, octadecyl, eicosyl, and the like; aryl radicals such as phenyl, naphthyl, biphenyl and the like; aralkyl radicals such as benzyl, phenylethyl, triphenylmethylethane and the like; alkaryl radicals such as tolyl, xylyl, and the like; and alicyclic radicals such as cyclopentyl, cyclohexyl, cyclooctyl, cyclohexylethyl, and the like. In addition such monovalent hydrocarbon radicals may be substituted with any substituent which does not unduly adversely effect the process of this invention. Suitable illustrative substituents that may be on the hydrocarbon radical are for example silyl radicals such as —Si(R$_9$)$_3$; amino radicals such as —N(R$_9$)$_2$; acyl radicals such as —C(O)R$_9$; carboxy radicals such as —C(O)OR$_9$, and acyloxy radicals such as —OC(O)R$_9$; amido radicals such as —C(O)N(R$_9$)$_2$ and —N(R$_9$)C(O)R$_9$; sulfonyl radicals such as —SO$_2$R$_9$; ether radicals such as —OR$_9$; thionyl ether radicals such as —SR$_9$ as well as halogen, nitro, cyano, trifluoromethyl and hydroxy radicals, and the like, wherein each R$_9$ individually represents the same or different substituted or unsubstituted monovalent hydrocarbon radical having the same meaning as defined for R$_1$ to R$_8$ above, with the proviso that in amino substituents such as —N(R$_9$)$_2$, each R$_9$ taken together can also represent a divalent organic bridging group that forms a heterocyclic radical with the nitrogen atom and in amido substituents such as —C(O)N(R$_9$)$_2$ and —N(R$_9$)C(O)R$_9$ each R$_9$ bonded to N can also be hydrogen. Illustrative substituted monovalent hydrocarbon radicals include e.g.

—(CH$_2$)$_2$Si(CH$_3$)$_3$, —(CH$_2$)$_3$Si(CH$_3$)$_3$,
—(CH$_2$)$_2$Si(C$_3$H$_7$)$_3$, —(CH$_2$)$_2$Si(C$_6$H$_5$)$_3$,
—(CH$_2$)$_2$C(O)CH$_3$, —(CH$_2$)C(O)C$_2$H$_5$,
—(CH$_2$)$_2$C(O)C$_6$H$_5$, —(CH$_2$)$_2$OC(O)C$_6$H$_5$,
—(CH$_2$)$_2$OC(O)CH$_3$, —(CH$_2$)$_2$N(C$_2$H$_5$)$_2$,

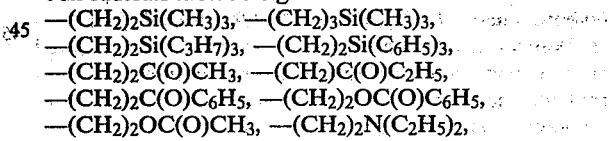

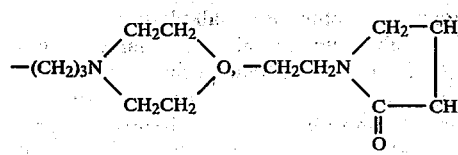

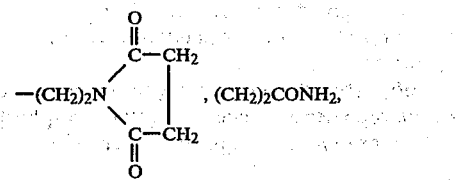

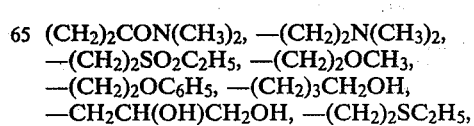

(CH$_2$)$_2$CON(CH$_3$)$_2$, —(CH$_2$)$_2$N(CH$_3$)$_2$,
—(CH$_2$)$_2$SO$_2$C$_2$H$_5$, —(CH$_2$)$_2$OCH$_3$,
—(CH$_2$)$_2$OC$_6$H$_5$, —(CH$_2$)$_3$CH$_2$OH,
—CH$_2$CH(OH)CH$_2$OH, —(CH$_2$)$_2$SC$_2$H$_5$,

—(CH₂)₃SC₆H₅, —(CH₂)₂N(CH₃)C(O)C₂H₅
as well as fluorophenyl, difluorophenyl, benzoyloxyphenyl, carboethoxyphenyl, acetylphenyl, ethoxyphenyl, phenoxyphenyl, hydroxyphenyl, carboxyphenyl, trifluoromethylphenyl, furyl, pyryl, methoxyethylphenyl, acetamidophenyl, dimethylcarbamylphenyl, and the like.

The more preferred substituted and unsubstituted monovalent hydrocarbon radicals represented by $R_1$ to $R_9$ are alkyl radicals having from 1 to 12 carbon atoms and aryl radicals having from 6 to 12 carbon atoms, the most preferred radicals being unsubstituted monovalent hydrocarbon radicals and the most preferred aryl radical being phenyl.

In general the more preferred organic tertiary bisphosphine starting materials as well as the more preferred organic tertiary bisphosphine monooxides are those such as (a) wherein $R_1$, $R_2$, $R_3$ and $R_4$ all represent an aryl radical; (b) wherein $R_1$ and $R_2$ both represent an aryl radical and $R_3$ and $R_4$ both represent an alkyl radical; (c) wherein $R_1$ and $R_3$ both represent an aryl radical and $R_2$ and $R_4$ both represent an alkyl radical; and (d) wherein $R_1$, $R_2$ and $R_3$ all represent an aryl radical and $R_4$ represents an alkyl radical.

The organic bridging group represented by Y in the above formulas is obviously a trivalent radical in the case of a being 1 and a divalent radical in the case of a being O, as well as a divalent radical in the case of b and/or d being 1. Such organic radicals may contain from 1 to 30 carbon atoms and can be selected from the group consisting of hydrocarbon radicals, oxygen containing hydrocarbon radicals (i.e. hydrocarbon radicals interrupted with an oxygen atom), sulfur containing hydrocarbon radicals (i.e. hydrocarbon radicals interrupted with a sulfur atom) and nitrogen containing hydrocarbon atoms (i.e. hydrocarbon radicals interrupted with a nitrogen atom). Preferably such radicals contain from 1 to 12 carbon atoms. Illustrative divalent hydrocarbon radicals include alkylene radicals (e.g. methylene (—CH₂—), ethylene, propylene, isopropylene, butylene, 1,2-dimethylethylene, t-butylene, neopentylene, 2-methylpropylene, hexylene, 2-ethylhexylene, dodecylene, eicosylene, and the like); arylene radicals (e.g. phenylene, diphenylene, and the like); as well as alkylene containing arylene radicals (e.g. methylenephenylene (—CH₂C₆H₄—), ethylenephenylethylene (C₂H₄C₆H₄—C₂H₄—), phenylenepropylphenylene (—C₆H₄—C(CH₃)₂—C₆H₄—), and the like); alkylidene radicals (e.g. ethylidene (—CH=CH—), and the like); and the like. Illustrative oxygen containing hydrocarbon radicals include alkyleneoxyalkylene radicals (e.g. ethyleneoxymethylene (—C₂H₄OCH₂—), propyleneoxymethylene (—C₃H₆OCH₂—), ethyleneoxyethylene (—C₂H₄OC₂H₄—), 1,2-bis(ethyleneoxy)ethane (—C₂H₄OC₂H₄OC₂H₄—), propyleneoxypropylene (—C₃H₆OC₃H₆—) and the like); aryleneoxyalkylene radicals (e.g. phenyleneoxymethylene (—C₆H₄OCH₂—), and the like); and the like. Illustrative sulfur or thio containing hydrocarbon radicals include alkylenethioalkylene radicals (e.g. ethylenethioethylene (—C₂H₄SC₂H₄—), 1,2-bis(ethylenethio)ethane (—C₂H₄SC₂H₄SC₂H₄—), propylenethiomethylene (—C₃H₆SCH₂—), propylenethiopropylene (—C₃H₆SC₃H₆—), and the like); arylenethioalkylene radicals (e.g. phenylenethiomethylene (—C₆H₄—S—CH₂—), and the like); and the like. Illustrative amino containing hydrocarbon radicals include alkyleneaminoalkylene radicals (e.g. methyleneaminomethylethylene (—CH₂N(CH₃)C₂H₄—), ethyleneaminomethylethylene (—C₂H₄N)(CH₃)C₂H₄—), 1,2-bis(ethyleneaminomethyl)ethane (—C₂H₄N(CH₃)C₂H₄N(CH₃)(C₂H₄—), propyleneaminomethylpropylene (—C₃H₆N(CH₃)C₃H₆—) and the like); and the like. Illustrative trivalent radicals include alkylene radicals such as

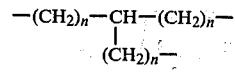

wherein each n individually has a value of from 0 to 6, more preferably from 1 to 4, and the like. Preferably Y is a divalent hydrocarbon radical, especially a divalent alkylene radical containing from 2 to 8 carbon atoms.

Illustrative examples of such organic tertiary polyphosphine starting materials include, e.g.
(C₆H₅)₂PCH₂P(C₆H₅)₂
(C₆H₅)₂P(CH₂)₂P(C₆H₅)₂
(C₆H₅)₂P(CH₂)₃P(C₆H₅)₂
(C₆H₅)₂P(CH₂)₄P(C₆H₅)₂
(C₆H₅)₂P(CH₂)₅P(C₆H₅)₂
(C₆H₅)₂P(CH₂)₆P(C₆H₅)₂
cis (C₆H₅)₂PCH=CHP(C₆H₅)₂
trans (C₆H₅)₂PCH=CHP(C₆H₅)₂
(C₆H₅)₂PCH(CH₃)CH₂P(C₆H₅)₂
(C₆H₅)₂PCH₂CH(CH₃)CH₂P(C₆H₅)₂
(C₆H₅)₂PCH₂CH₂CH(CH₃)CH₂CH₂P(C₆H₅)₂
(C₆H₅)₂PCH₂C(CH₃)₂CH₂P(C₆H₅)₂
(C₆H₅)(CH₃)PCH₂P(CH₃)(C₆H₅)
(C₆H₅)(CH₃)P(CH₂)₂P(CH₃)(C₆H₅)
(C₆H₅)(CH₃)P(CH₂)₃P(CH₃)(C₆H₅)
(C₆H₅)(C₂H₅)P(CH₂)₂P(C₂H₅)(C₆H₅)
(C₆H₅)(C₃H₇)P(CH₂)₂P(C₃H₇)(C₆H₅)
(C₆H₅)(C₆H₁₃)P(CH₂)₂P(C₆H₁₃)(C₆H₅)
C₆H₅(C₆H₁₁)P(CH₂)₂P(C₆H₁₁)(C₆H₅)
C₆H₅(C₄H₉)P(CH₂)₂P(C₄H₉)(C₆H₅)
(C₆H₅)(CH₃C₆H₄)P(CH₂)₂P(C₆H₄CH₃)(C₆H₅)
(CH₃C₆H₄)₂P(CH₂)₂P(C₆H₄CH₃)₂
(C₆H₅)₂P(CH₂)₂O(CH₂)₂P(C₆H₅)₂
(C₆H₅)(CH₃)P(CH₂)₃S(CH₂)₃P(C₆H₅)(CH₃)
(C₆H₅)₂P(CH₂)₂N(CH₃)(CH₂)₂P(C₆H₅)₂
(C₂H₅)₂P(CH₂)₃P(C₂H₅)₂
(C₆H₅)₂P(CH₂)₂P[(CH₂)₂Si(CH₃)₃]₂
(C₆H₅)₂P(CH₂)₂P[CH₂C(CH₃)₃]₂
(C₆H₅)₂P(CH₂)₂P[CH₂CH₂C(CH₃)₃]₂
(C₆H₅)₂PCH₂P(CH₃)₂
(C₆H₅)₂PCH₂P(C₂H₅)₂
(C₆H₅)₂P(CH₂)₂P(C₂H₅)₂
(C₆H₅)₂P(CH₂)₂P(C₃H₇)₂
(C₆H₅)₂P(CH₂)₃P(C₄H₉)₂
(C₆H₅)₂P(CH₂)₃P(C₅H₁₁)₂
(C₆H₅)₂P(CH₂)₂P(C₆H₁₃)₂
(C₆H₅)₂P(CH₂)₄P(C₂H₅)₂
(C₆H₅)₂P(CH₂)₅P(C₂H₅)₂
(C₆H₅)₂P(CH₂)₂P[(CH₂)₂C(O)CH₃]₂
(C₆H₅)₂P(CH₂)₂P[(CH₂)₂OC(O)CH₃]₂
(C₆H₅)₂P(CH₂)₂P[(CH₂)₂N(C₂H₅)₂]₂

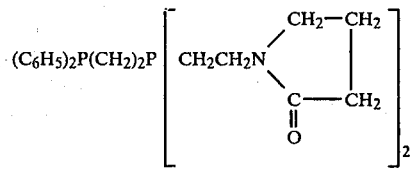

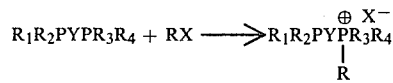

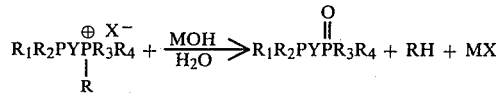

$(C_6H_5)_2P(CH_2)_2P[(CH_2)_2CONH_2]_2$
$(C_6H_5)_2P(CH_2)_2P[(CH_2)_2SO_2C_2H_5]_2$
$(C_6H_5)_2P(CH_2)_2P[(CH_2)_2OCH_3]_2$
$(C_6H_5)_2P(CH_2)_2P[(CH_2)_3CH_2OH]_2$
$(C_6H_5)_2P(CH_2)_2P[(CH_2)_2SC_2H_5]_2$
$(C_6H_5)_2P(CH_2)_2P[(CH_2)_2N(CH_3)COC_2H_5]_2$
$(C_6H_5)_2P(CH_2)_2P(C_6H_5)(CH_2)_2P(C_6H_5)_2$
$[(C_6H_5)_2PCH_2CH_2]_3CH$
$[(C_6H_5)_2PCH_2CH_2]_3P$
and the like.

The organic monofunctional alkylating agent starting materials employable in the process of this invention include any suitable alkylating agent capable of reacting with the tertiary polyphosphine starting material and forming a monophosphonium salt thereof. Such alkylating agents are normally liquids and preferably should have a high miscibility with the solvent employed. Illustrative organic monofunctional alkylating agents include e.g. monovalent hydrocarbon halides, and the like, where the monovalent hydrocarbon radical can contain from 1 to 30 carbon atoms and is preferably an alkyl, aryl, aralkyl, alkaryl, or cycloalkyl radical. Such organic monofunctional alkylating agents and/or methods for their preparation are well known and include for example, $CH_3I$, $CH_3Br$, $CH_3Cl$, $C_2H_5Br$, $C_2H_5I$, $C_2H_5Cl$, $CH_3I$, $C_3H_7Br$, $C_3H_7Cl$, $C_6H_5CH_2I$, $C_6H_5CH_2Br$, $C_6H_5CH_2Cl$, $C_6H_5C_2H_5I$, $C_6H_5C_2H_4Br$, $C_6H_5C_2H_4Cl$, and the like. The preferred monofunctional alkylating agents are monovalent hydrocarbon halides (e.g. chlorides, bromides and iodides), especially alkyl and aralkyl halides having from 1 to 10 carbon atoms. The most preferred monofunctional alkylating agent is benzyl bromide.

Since the reaction of step one of the process of this invention is a stoichiometric type reaction it is preferred to employ about one mole of monofunctional alkylating agent per mole of the tertiary polyphosphine starting material. However, lower or higher amounts of the alkylating agent can be employed if desired. Of course it is understood that the use of lower amounts of the alkylating agent may lead to a decrease in the yield of the monophosphonium salt desired along with more unreacted polyphosphine starting material, while higher amounts of the alkylating agent may lead to the production of undesirable diphosphonium salts. In general amounts of monofunctional alkylating agent ranging from about 0.5 to about 1.5 moles per mole of polyphosphine starting material should be sufficient for most purposes.

It should be noted that the particular monofunctional alkylating agent and/or particular polyphosphine starting material employed in a given process can be very important. For example, while the subject preferred two-step process of this invention can be generally depicted by the following illustrative equations:

wherein RX represents a monofunctional alkylating agent and MOH represents the alkaline material of the aqueous alkaline solution; the particular phosphorus atom of the polyphosphine starting material that is alkylated to form the monophosphonium salt and/or the substituent radicals on the phosphorus oxide group (P=O) of the polyphosphine monooxide product in a given process may be governed by the particular polyphosphine starting material employed. For instance different substituent radicals may have different degrees of affinity (i.e. bonding strengths) for a phosphorus atom, e.g. an alkylphosphorus bond (e.g. $CH_3$—P) being stronger than a phenylphosphorus ($C_6H_5$—P) bond which in turn is stronger than a benzylphosphorus ($C_6H_5CH_2$—P) bond. Consequently employing an alkylating agent that will provide a monophosphonium salt in which the alkylating radical of the alkylating agent is not bonded to the alkylated phosphorus atom of said salt as strongly as any of the starting material substituent radicals present on said alkylated phosphorus atom will lead to a polyphosphine monooxide product upon hydrolysis in which the substituent radicals on the phosphorus oxide group of said product correspond to those starting material radicals on the alkylated phosphorus atom of the monophosphonium salt as seen e.g. by the following illustrative reaction:

Scheme I

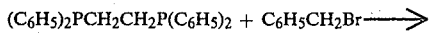

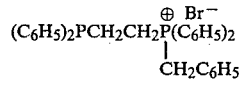

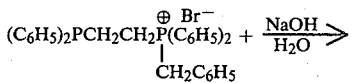

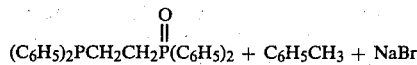

Conversely, employing an alkylating agent that will provide a monophosphine salt in which the alkylating radical of the alkylating agent is bonded to the alkylated phosphorus atom of said salt more strongly than any of the starting material substituent radicals present on said alkylated phosphorus atom will lead to a polyphosphine monooxide product upon hydrolysis in which one of the substituent radicals on the phosphorus oxide group of said product represents the alkylating radical of the alkylating agent employed which has replaced the weaker of the two starting material substituent radicals on the alkylated phosphorus atom of the monophosphonium salt as seen e.g. by the following illustrative reaction:

Scheme II

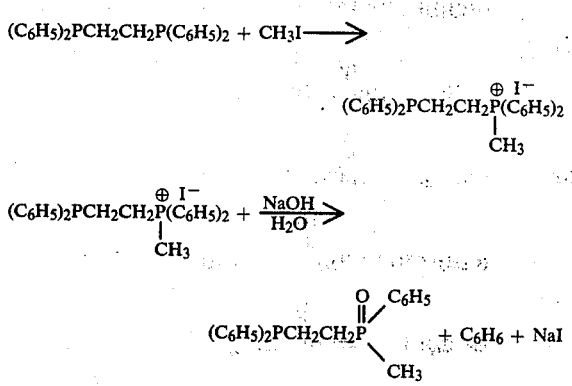

Of course it is to be understood that the difference in substituent affinity that various radicals have for phosphorus is a beneficial feature of the subject process of this invention, since it provides a wide degree of processing latitude for the production of the various organic tertiary polyphosphine monooxides that may be desired. For example such processing latitude affords a facile method for preparing desired bisphosphine monooxide products that correspond to their readily available bisphosphine starting materials (e.g., by Scheme I above), as well as a facile method for preparing certain desired bisphosphine monooxide products even if their corresponding bisphosphine starting materials are not readily available by simply employing a different starting material that may be more readily available and converting it to the bisphosphine monooxide product desired (e.g. by Scheme II, above).

Moreover it is believed that due to the electron rich nature of various phosphine bonded radicals, e.g. alkyl radicals rendering a phosphorus atom more nucleophilic than aryl groups, that the organic monofunctional alkylating agent employed in step one of the process of this invention will have a greater affinity for reacting with the phosphorus atom that contains the greater number of alkyl radicals in the polyphosphine starting material. Thus if non-symmetrical polyphosphine starting materials are employed (i.e. polyphosphines wherein the substituent groups on at least one phosphorus atom thereof are not the same as the substituent groups on at least one other phosphorus atom thereof such as e.g. bisphosphines wherein the $R_1R_2P$ and $R_3R_4P$ groups are not identical but different from one another), the monophosphonium salt so produced may be a mixture of different monophosphonium salts which upon hydrolysis may result in a mixture of polyphosphine monooxides e.g. bisphosphines such as

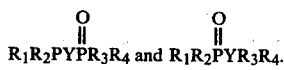

However it is believed that the far more predominate monophosphonium salt (at least over 50 percent by weight of the salt product produced) in such a mixture will be that monophosphonium salt in which the phosphorus atom that has been alkylated by the alkylating agent will correspond to that phosphorus atom in the non-symmetrical polyphosphine starting material that contains the higher number of stronger phosphorus nucleophilic rendering substituents e.g. the most alkyl substituents as compared to aryl substituents. On the other hand essentially no such monooxide product mixture can occur when the polyphosphine starting material employed is symmetrical (i.e. polyphosphines wherein the substituents on each phosphorus atom thereof are the same as the substituents on each other phosphorus atom thereof such as e.g. bisphosphines wherein the $R_1R_2P$ and $R_3R_4P$ groups are identical and correspond to one another. In such cases a highly selective essentially quantitative amount of a single desired polyphosphine monooxide compound can be produced by the process of this invention.

Thus it is to be understood that the polyphosphine monooxide product of the process of this invention may consist essentially of a single polyphosphine monooxide compound or a mixture of different individual polyphosphine monooxide compounds and that the monooxides of such mixtures can be easily separated if desired by any suitable method such as by fractional crystallization, distillation, and the like. Moreover it is to be further understood that different degrees in affinity (bonding strengths) between various substituent radicals and phosphorus, as well as different degrees in electron rich natures between various phosphorus bonded substituent radicals can easily be determined by a few routine preliminary experiments that are well within the ability of those skilled in the art thus providing one with excellent control over the direction of the process of this invention.

Step two of the process of this invention involves the subsequent hydrolysis of the recovered monophosphonium salt produced according to step one with an aqueous alkaline solution. The hydrolysis is a facile and quantitative reaction which results in the formation of the desired organic tertiary polyphosphine monooxide product. The organic tertiary polyphosphine monooxides are air stable solids which can be easily isolated and recovered from the aqueous reaction product mixture by any suitable conventional method such as by filtration, and the like. The desired polyphosphine monooxide product, if desired, can then be washed with water to remove excess base, dried and even recrystallized, if desired, in any conventional manner, such as with an alcohol, to yield highly chemically pure samples of organic tertiary polyphosphine monooxide.

The hydrolysis reaction may be carried out in any suitable conventional hydrolysis manner and merely involves hydrolyzing the intermediate monophosphonium salt (a wetable, but insoluble powder) into a different solid, i.e. the desired organic tertiary polyphosphine monooxide which is non-wetable and hydrophobic.

The hydrolysis conditions are not narrowly critical and can be varied widely with regard to the reaction temperature, concentrations and types of reactants employed.

Suitable alkaline materials for the aqueous alkaline solution include e.g. any of the Group Ia and Group IIa conventional bases e.g. hydroxides and carbonates. Illustrative examples of such bases are e.g. the alkali metal, alkaline earth metal and ammonium hydroxides and carbonates, such as sodium bicarbonate, sodium carbonate, sodium hydroxide, potassium hydroxide, lithium hydroxide, cesium hydroxide, barium hydroxide, calcium hydroxide, ammonium hydroxide, and the like. The preferred alkaline material is sodium hydroxide.

The alkaline base material is a scavenger for the anion of the monophosphonium salt. Of course while lower or higher amounts of the alkaline material (up to the limit of the solubility of the particular alkaline material employed) in relation to at least that stoichiometric equivalent amount of alkaline material that might be necessary to scavenge all of the anion present in the monophosphonium salt to be hydrolyzed can be employed, it is preferred to employ an excess of such a stoichiometric equivalent amount of alkaline material in order to obtain the optimum yield of polyphosphine monooxide desired. Thus the concentration of the alkaline material in the aqueous solution may vary from about 0.1 weight percent up to 30 weight percent, or higher. In general aqueous alkaline solutions containing alkaline concentrations of from about 1 to 20 percent by weight and preferably from about 5 to 10 percent by weight should be sufficient for most purposes. Likewise the amount of water employed is not narrowly critical and obviously need only be at least that amount of water necessary to hydrolyze the monophosphonium salt to its desired polyphosphine monooxide product. In general it is preferred to employ an excess of such a stoichiometric amount of water. Thus amounts of water ranging from about a 100 percent stoichiometric excess on up to about a 10,000 percent stoichiometric excess or higher may be employed. The most preferred amount of water can of course be determined by routine experimentation.

The hydrolysis reaction of step two of the process of this invention can be carried out at any suitable temperature which generally depends merely on the reactivity of the intermediate monophosphonium salt. Thus the hydrolysis can be carried out at sub, atmospheric or elevated pressures, as desired and in any suitable reaction vessel. In general most monophosphonium salts should hydrolyze readily under ambient temperature conditions. Thus temperatures ranging from about 20° C. to about 100° C. should be suitable for most instances. Moreover, while the hydrolysis can be carried out in air, it is preferably carried out in an inert gas atmosphere, such as nitrogen, in order to avoid air oxidation of the polyphosphine. It is further preferred to thoroughly mix the reactants involved and such can be done by any conventional means such as by stirring, and the like. The general hydrolysis reaction is quite rapid and its progress and completion followed in any suitable manner such as by thin layer chromatography and by the consumption of the phosphine salt starting material, as witnessed by the formation of the desired organic tertiary polyphosphine monooxide solid which can be easily recovered as described above.

Illustrative organic tertiary polyphosphine monooxides that may be derived by the process of this invention include, e.g.

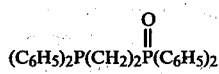

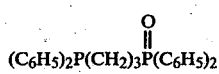

-continued

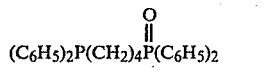

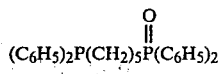

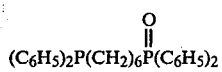

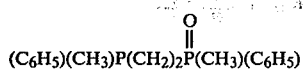

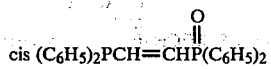

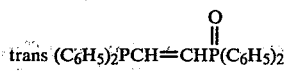

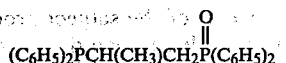

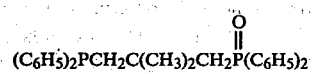

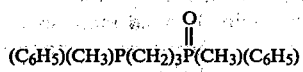

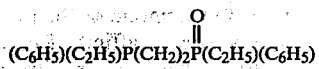

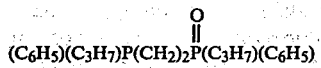

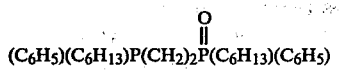

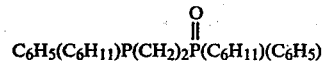

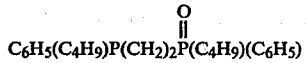

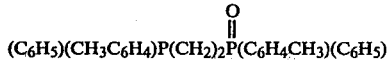

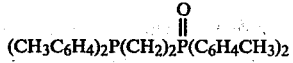

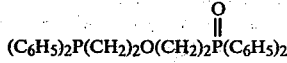

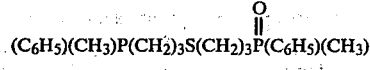

-continued $(C_6H_5)_2\overset{O}{\overset{\|}{P}}(CH_2)_2N(CH_3)(CH_2)_2P(C_6H_5)_2$ $(C_2H_5)_2\overset{O}{\overset{\|}{P}}(CH_2)_3P(C_2H_5)_2$ $(C_6H_5)_2\overset{O}{\overset{\|}{P}}(CH_2)_2P[(CH_2)_2Si(CH_3)_3]_2$ $(C_6H_5)_2\overset{O}{\overset{\|}{P}}(CH_2)_2P[CH_2C(CH_3)_3]_2$ $(C_6H_5)_2\overset{O}{\overset{\|}{P}}(CH_2)_2P[CH_2CH_2C(CH_3)_3]_2$ $(C_6H_5)_2\overset{O}{\overset{\|}{P}}CH_2P(CH_3)_2$ $(C_6H_5)_2\overset{O}{\overset{\|}{P}}CH_2P(C_2H_5)_2$ $(C_6H_5)_2\overset{O}{\overset{\|}{P}}(CH_2)_2P(C_2H_5)_2$ $(C_6H_5)_2\overset{O}{\overset{\|}{P}}(CH_2)_2P(C_3H_7)_2$ $(C_6H_5)_2\overset{O}{\overset{\|}{P}}(CH_2)_3P(C_4H_9)_2$ $(C_6H_5)_2\overset{O}{\overset{\|}{P}}(CH_2)_3P(C_5H_{11})_2$ $(C_6H_5)_2\overset{O}{\overset{\|}{P}}(CH_2)_2P(C_6H_{13})_2$ $(C_6H_5)_2\overset{O}{\overset{\|}{P}}(CH_2)_4P(C_3H_7)_2$ $(C_6H_5)_2\overset{O}{\overset{\|}{P}}(CH_2)_5P(C_3H_7)_2$ $(C_6H_5)_2\overset{O}{\overset{\|}{P}}(CH_2)_2P[(CH_2)_2C(O)CH_3]_2$ $(C_6H_5)_2\overset{O}{\overset{\|}{P}}(CH_2)_2P[(CH_2)_2OC(O)CH_3]_2$ $(C_6H_5)_2\overset{O}{\overset{\|}{P}}(CH_2)_2P[(CH_2)_2N(C_2H_5)_2]_2$ $(C_6H_5)_2\overset{O}{\overset{\|}{P}}(CH_2)_2P\left[\begin{array}{c}CH_2CH_2N\diagup_{\diagdown}^{CH_2-CH_2}\diagdown_{\diagup}^{C-CH_2}\\ \overset{\|}{O}\end{array}\right]_2$ $(C_6H_5)_2\overset{O}{\overset{\|}{P}}(CH_2)_2P[(CH_2)_2CONH_2]_2$ $(C_6H_5)_2\overset{O}{\overset{\|}{P}}(CH_2)_2P[(CH_2)_2SO_2C_2H_5]_2$ -continued $(C_6H_5)_2\overset{O}{\overset{\|}{P}}(CH_2)_2P[(CH_2)_2OCH_3]_2$ $(C_6H_5)_2\overset{O}{\overset{\|}{P}}(CH_2)_2P[(CH_2)_3CH_2OH]_2$ $(C_6H_5)_2\overset{O}{\overset{\|}{P}}(CH_2)_2P[(CH_2)_2SC_2H_5]_2$ $(C_6H_5)_2\overset{O}{\overset{\|}{P}}(CH_2)_2P[(CH_2)_2N(CH_3)COC_2H_5]_2$ $(C_6H_5)_2\overset{O}{\overset{\|}{P}}(CH_2)_2P(C_6H_5)(CH_2)_2P(C_6H_5)_2$ $[(C_6H_5)_2PCH_2CH_2]_2CH[CH_2CH_2\overset{O}{\overset{\|}{P}}(C_6H_5)_2]$ $[(C_6H_5)_2PCH_2CH_2]_3\overset{O}{\overset{\|}{P}}$ $(C_6H_5)_2\overset{O}{\overset{\|}{P}}(CH_2)_4P(C_2H_5)_2$ $(C_6H_5)_2\overset{O}{\overset{\|}{P}}(CH_2)_5P(C_2H_5)_2$, and the like.

The organic tertiary polyphosphine monooxide products of this invention have a wide range of utility e.g. as phosphorus ligands for homogeneous transition metal catalyzed processes such as in the hydrogenation and hydroformylation of unsaturated compounds (e.g. olefins) to produce aldehydes and alcohols, the carbonylation of alcohols to produce acids, the homologation of alcohols to produce higher alcohols, and the like, as illustrated, e.g., in assignee's concurrently filed U.S. Patent Application Ser. No. 293,190 entitled, "Hydroformylation Process Using Bisphosphine Monooxide Ligands", the entire disclosure of which is incorporated herein by reference thereto.

The following examples are illustrative of the present invention and are not to be regarded as limitative. It is to be understood that all parts, percentages and proportions referred to herein and in the appended claims are by weight unless otherwise indicated.

EXAMPLES 1-6

A series of organic ditertiary bisphosphine monooxides were prepared from different bisphosphine starting materials by following the general procedure described below.

Step One

A dry one-liter three-neck flask, equipped with a mechanical stirrer, thermometer, nitrogen inlet and condenser, which was kept under nitrogen was successively charged with an organic ditertiary bisphosphine dissolved in dry, degassed toluene followed by benzylbromide. Equimolar amounts of bisphosphine and benzylbromide and 500 ml. of toluene per 0.1 mole of the bisphosphine starting material were employed in each instance. The mixture was then heated to about 80° C. and a white monophosphonium salt precipitate soon formed. The progress was followed by thin layer chromatography and by monitoring the consumption of the ditertiary bisphosphine starting material. Upon completion of the reaction (about six to eight hours) the reaction mixture was allowed to cool to room temperature and the formed solid monophosphonium salt filtered therefrom. The monophosphonium salt was then washed with three 50 ml. portions of toluene and dried under vacuum.

Step Two

The monophosphonium salt produced according to step one above was then charged to a three-neck flask equipped with a mechanical stirrer, thermometer, nitrogen inlet and condenser which was kept under nitrogen, followed by a degassed solution of 10 percent by weight sodium hydroxide in water. A 500 ml. of the aqueous sodium hydroxide solution per 0.1 mole of the monophosphonium salt was employed in each instance. The mixture was then stirred vigorously for two hours and gently heated at 50° to 60° C. with a water bath. Under these conditions the starting solid monophosphonium salt (a wettable, but insoluble powder) was hydrolyzed into a different solid i.e. a non-wettable hydrophobic organic ditertiary bisphosphine monooxide solid. Upon cooling to room temperature the bisphosphine monoxide product was then recovered by filtration, washed with large amounts of water to remove any excess sodium hydroxide, dried under vacuum and recrystallized from isopropanol.

The starting organic ditertiary bisphosphine used in each instance, its intermediate monophosphonium salt and corresponding organic ditertiary bisphosphine monoxide product are given in Table I below.

TABLE I

| Example No. | Bisphosphine (grams) | Benzyl Bromide (grams) | Monophosphonium Salt | Biosphosphine (grams) | Monooxide | GRAMS Crude | Recrystalized |
|---|---|---|---|---|---|---|---|
| 1. | $(C_6H_5)_2PCH_2P(C_6H_5)_2$ (76.88 g.) | 34.21 g. | $(C_6H_5)_2\overset{\oplus}{P}CH_2P(C_6H_5)_2 \; Br^-$ <br> $\vert$ <br> $CH_2C_6H_5$ | 103.65 g. | $(C_6H_5)_2PCH_2\overset{O}{\overset{\parallel}{P}}(C_6H_5)_2$ | 50.1 g. | 42.03 g. |
| 2. | $(C_6H_5)_2P(CH_2)_2P(C_6H_5)_2$ (79.6 g.) | 34.21 g. | $(C_6H_5)_2P(CH_2)_2\overset{\oplus}{P}(C_6H_5)_2 \; Br^-$ <br> $\vert$ <br> $CH_2C_6H_5$ | 106.07 g. | $(C_6H_5)_2P(CH_2)_2\overset{O}{\overset{\parallel}{P}}(C_6H_5)_2$ | — | 66.98 g. |
| 3. | $(C_6H_5)_2P(CH_2)_3P(C_6H_5)_2$ (58.68 g.) | 24.35 g. | $(C_6H_5)_2P(CH_2)_3\overset{\oplus}{P}(C_6H_5)_2 \; Br^-$ <br> $\vert$ <br> $CH_2C_6H_5$ | 70.52 g. | $(C_6H_5)_2P(CH_2)_3\overset{O}{\overset{\parallel}{P}}(C_6H_5)_2$ | — | 46.3 g. |
| 4. | $(C_6H_5)_2P(CH_2)_4P(C_6H_5)_2$ (85.2 g.) | 34.2 g. | $(C_6H_5)_2P(CH_2)_4\overset{\oplus}{P}(C_6H_5)_2 \; Br^-$ <br> $\vert$ <br> $CH_2C_6H_5$ | 103.43 g. | $(C_6H_5)_2P(CH_2)_4\overset{O}{\overset{\parallel}{P}}(C_6H_5)_2$ | 73.4 g. | 66.81 g. |
| 5. | $(C_6H_5)_2P(CH_2)_5P(C_6H_5)_2$ (33.5 g.) | 13.02 g. | $(C_6H_5)_2P(CH_2)_5\overset{\oplus}{P}(C_6H_5)_2 \; Br^-$ <br> $\vert$ <br> $CH_2C_6H_5$ | 33.72 g. | $(C_6H_5)_2P(CH_2)_5\overset{O}{\overset{\parallel}{P}}(C_6H_5)_2$ | — | 24.1 g. |
| 6. | $(C_6H_5)_2P(CH_2)_6P(C_6H_5)_2$ (23.25 g.) | 8.76 g. | $(C_6H_5)_2P(CH_2)_6\overset{\oplus}{P}(C_6H_5)_2 \; Br^-$ <br> $\vert$ <br> $CH_2C_6H_5$ | 24.53 g. | $(C_6H_5)_2P(CH_2)_6\overset{O}{\overset{\parallel}{P}}(C_6H_5)_2$ | 15.7 g. | 14.5 g. |

EXAMPLES 7-8

By following the procedure outlined in Examples 1–7, cis and trans bisphosphine starting materials of the formula $(C_6H_5)_2PCH=CHP(C_6H_5)_2$ were reacted with benzylbromide to form their corresponding monophosphonium salts, which were then hydrolyzed to produce the corresponding cis and trans bisphosphine monooxide products of the formula:

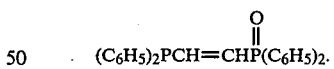

$$(C_6H_5)_2PCH=CHP(O)(C_6H_5)_2.$$

The structure of each bisphosphine monooxide product of Examples 1 to 8 above was confirmed and characterized by their Phosphorus-31 Nmr, Infrared and Mass Spectra Data as shown in Table II below.

TABLE II

| | Phosphorus - 31 Nmr, Infrared and Mass Spectra Data | | | | |
|---|---|---|---|---|---|
| Example No. | Bisphosphine Monooxide Product | $\delta^a$ P | $\delta^a$ P=O | $J^b$ P—P | m/e$^c$ |
| 1. | $(C_6H_5)_2PCH_2P(O)(C_6H_5)_2$ | −28.73 | 27.24 | 49.5 | 400(416) |
| 2. | $(C_6H_5)_2P(CH_2)_2P(O)(C_6H_5)_2$ | −12.41 | 31.65 | 48.3 | 414(430) |
| 3. | $(C_6H_5)_2P(CH_2)_3P(O)(C_6H_5)_2$ | −18.60 | 29.84 | 0 | 428(444) |
| 4. | $(C_6H_5)_2P(CH_2)_4P(O)(C_6H_5)_2$ | −16.98 | 30.08 | 0 | 442(458) |
| 5. | $(C_6H_5)_2P(CH_2)_5P(O)(C_6H_5)_2$ | −16.27 | 31.30 | 0 | 456(472) |
| 6. | $(C_6H_5)_2P(CH_2)_6P(O)(C_6H_5)_2$ | −16.55 | 30.73 | 0 | 470(486) |
| 7. | $(C_6H_5)_2PCH=CHP(O)(C_6H_5)_2$ cis | −18.87 | 34.00 | 24.4 | 412(428) |
| 8. | $(C_6H_5)_2PCH=CHP(O)(C_6H_5)_2$ | −5.76 | 21.43 | 19.6 | 412(428) |

TABLE II-continued

Phosphorus - 31 Nmr, Infrared and Mass Spectra Data

| Example No. | Bisphosphine Monooxide Product | $\delta^a$ P | $\delta^a$ P=O | $J^b$ P—P | m/e$^c$ |
|---|---|---|---|---|---|
| | trans | | | | |

$^a$Chemical shifts in ppm relative to external phosphoric acid. Solvent: methylene chloride. The minus sign denotes upfield shifts relative to phosphoric acid.
$^b$Long range P—P coupling constant in Hertz.
$^c$Parent ions, obtained by chemical ionization mass spectrometry using isobutane as ionization gas. In parenthesis are the parent ions of traces of respective bis-phosphine dioxides.

Various modifications and variations of this invention will be obvious to a worker skilled in the art and it is to be understood that such modifications and variations are to be included within the preview of this application and the spirit and scope of the appended claims.

What is claimed is:

1. A process for producing an organic tertiary polyphosphine monooxide which comprises reacting an organic tertiary polyphosphine compound having the general formula

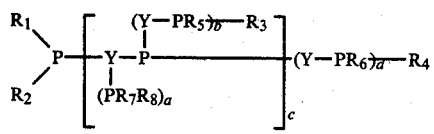

wherein each $R_1$, $R_2$, $R_3$, $R_4$, $R_5$, $R_6$, $R_7$ and $R_8$ represent an identical or different, substituted or unsubstituted monovalent hydrocarbon radical containing from 1 to 30 carbon atoms, wherein each Y represents an identical or different organic bridging group containing from 1 to 30 carbon atoms selected from the group consisting of hydrocarbon radicals, oxygen containing hydrocarbon radicals, nitrogen containing hydrocarbon radicals and sulfur containing hydrocarbon radicals, wherein a, b and d each represent a value of zero or 1, and wherein c represents an integer of from 1 to 3; with an organic monofunctional alkylating agent containing from 1 to 30 carbon atoms selected from the group consisting of monovalent hydrocarbon halides and monovalent hydrocarbon sulfates, in the presence of an inert organic solvent for said organic tertiary polyphosphine compound to form an insoluble monophosphonium salt of said organic tertiary polyphosphine compound; hydrolyzing said salt compound with an aqueous alkaline solution to form an organic tertiary polyphosphine monooxide product wherein the oxygenated phosphorous atom of said monooxide product corresponds to the alkylated phosphorus atom of said monophosphonium salt, and recovering the monooxide product so produced.

2. A process as defined in claim 1 wherein the organic tertiary polyphosphine compound is a polyphosphine having a formula selected from the group consisting of $R_1R_2PYPR_3R_4$,

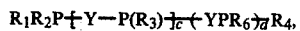

$R_1R_2P—Y—P(YPR_5R_3)(YPR_6R_4)$, and

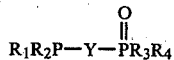

$$R_1R_2P—Y—PR_3R_4;$$
$$\quad\quad\quad\quad\quad |$$
$$\quad\quad\quad\quad PR_7R_8$$

wherein each $R_1$ to $R_8$ radical represents an identical or different, substituted or unsubstituted monovalent hydrocarbon radical selected from the group consisting of alkyl radicals containing from 1 to 12 carbon atoms and aryl radicals containing from 6 to 12 carbon atoms, wherein c has a value of 1 to 3 and d has a value of 1, wherein Y is an alkylene bridging group containing from 2 to 8 carbon atoms, and wherein said alkylating agent is a monovalent hydrocarbon halide containing from 1 to 10 carbon atoms selected from the group consisting of alkyl chlorides, alkyl bromides, alkyl iodides, aralkyl chlorides, aralkyl bromides and aralkyl iodides.

3. A process as defined in claim 2, wherein a organic tertiary bisphosphine monooxide having the formula $$\overset{O}{\underset{\|}{R_1R_2P—Y—PR_3R_4}}$$

is produced by employing as the organic tertiary polyphosphine starting material a bisphosphine compound having the formula $R_1R_2P—Y—PR_3R_4$.

4. A process as defined in claim 3, wherein $R_1$, $R_2$, $R_3$ and $R_4$ are unsubstituted monovalent hydrocarbon radicals.

5. A process as defined in claim 4, wherein $R_1$, $R_2$, $R_3$ and $R_4$ are selected from the group consisting of alkyl and phenyl radicals.

6. A process as defined in claim 5, wherein $R_1$, $R_2$, $R_3$ and $R_4$ are phenyl radicals.

7. A process as defined in claim 5, wherein the monovalent alkylating agent is benzyl bromide.

8. A process as defined in claim 6 wherein the monovalent alkylating agent is benzyl bromide.

9. A process as defined in claim 2 wherein the organic solvent employed is an inert hydrocarbon solvent in which the organic tertiary polyphosphine is soluble, the monofunctional alkylating agent miscible and the monophosphonium salt insoluble.

10. A process as defined in claim 9, wherein both the reaction to produce the monophosphonium salt and the reaction to produce the polyphosphine monooxide product are carried out in an inert gas atmosphere, and wherein the aqueous alkaline solution employed is an aqueous solution of an alkaline material selected from the group consisting of alkali metal, alkali earth metal and ammonium hydroxides and carbonates.

11. A process as defined in claim 10, wherein the aqueous alkaline solution is aqueous sodium hydroxide.

* * * * *